United States Patent [19]

Findeisen

[11] 4,267,365
[45] May 12, 1981

[54] PROCESS FOR THE PREPARATION OF OLIGOMERIC ACRYLIC ACIDS

[75] Inventor: Kurt Findeisen, Odenthal, Fed. Rep. of Germany

[73] Assignee: Bayer Aktiengesellschaft, Leverkusen, Fed. Rep. of Germany

[21] Appl. No.: 973,342

[22] Filed: Dec. 26, 1978

[30] Foreign Application Priority Data

Jan. 5, 1978 [DE] Fed. Rep. of Germany ....... 2800357

[51] Int. Cl.³ .......................................... C07C 69/52
[52] U.S. Cl. .................................. 560/205; 156/326; 156/327; 526/317; 562/598
[58] Field of Search ............... 156/326, 327; 428/500; 526/317; 562/512, 588, 587, 598; 203/8; 560/205

[56] References Cited

U.S. PATENT DOCUMENTS

| | | | |
|---|---|---|---|
| 2,141,546 | 12/1938 | Strain | 526/317 |
| 2,806,878 | 9/1957 | Luberoff | 562/598 |
| 3,227,628 | 1/1966 | Hess | 562/598 |
| 3,818,079 | 6/1974 | Sato et al. | 562/598 |
| 3,868,410 | 2/1975 | Horlenko et al. | 562/598 |
| 3,888,922 | 6/1975 | Levy et al. | 562/598 |
| 3,948,867 | 4/1976 | Bäder et al. | 526/317 |
| 4,117,235 | 9/1978 | Taylor | 560/205 |

FOREIGN PATENT DOCUMENTS 971055 9/1964 United Kingdom ..................... 526/317
1256428 12/1971 United Kingdom ..................... 560/205

*Primary Examiner*—John J. Gallagher
*Attorney, Agent, or Firm*—Sprung, Felfe, Horn, Lynch & Kramer

[57] ABSTRACT

A process for the preparation of an oligomeric acrylic acid of the formula $$CH_2=CH-COO[CH_2-CH_2-COO]_nH$$

wherein n represents a number from 1 to 6 is described wherein acrylic acid is heated in the presence of a polymerization inhibitor to a temperature of about 50° to about 200° C. The process can be carried out at subatmospheric pressure, atmospheric pressure or superatmospheric pressure and in the presence or absence of a solvent.

7 Claims, No Drawings

PROCESS FOR THE PREPARATION OF OLIGOMERIC ACRYLIC ACIDS

The invention relates to a process for the preparation of oligomeric acrylic acids by thermal treatment of acrylic acid.

It is known that β-acryloyloxy-propionic acid can be obtained by heating acrylic acid in furan for five hours in a bomb tube to 160° C. (J. Gen. Chem. USSR, 8, 22–34 (1938)).

Further, it is known that β-acryloyloxy-propionic acid can be prepared by heating acrylic acid in the presence of ammonia or amines at temperatures of 50° to 300° C., if appropriate under elevated pressure (Japanese Published Specification No. 85,020/1974).

A process has been found for the preparation of oligomeric acrylic acids of the formula (I)

$$CH_2=CH-COO[CH_2-CH_2-COO]_nH \qquad (I)$$

in which
n represents a number from 1 to 6, which is characterised in that acrylic acid is heated, in the presence of 0.001 to 1% by weight of a polymerization inhibitor, if appropriate under elevated pressure and, if appropriate, in the presence of an inert solvent, to a temperature in the range from about 50° to 200° C.

Suitable polymerization inhibitors are commercial compounds, such as are known, to those skilled in the art, for the purpose of avoiding undesired polymerizations of olefinic double bonds. As examples of such inhibitors there can be mentioned: molecular oxygen and hence also oxygen-containing air, nitric oxide, phenols, such as hydroquinone or tert.-butyl-pyrocatechol, quinones, aromatic amines, such as N-phenyl-β-naphthylamine or derivatives of p-phenylenediamine, phenothiazine, methylene blue, nitro compounds, some sulphur compounds and stable radicals such as diphenylpicrylhydrazyl (Vieweg/Braun, Kunststoff-Handbuch (Plastics Handbook), Volume 1, Carl Hanser Verlag, Munich 1975, page 47).

The polymerization inhibitors are employed in the process according to the invention in an amount of 0.001 to 1% by weight, preferably in an amount of 0.002 to 0.1% by weight, relative to the amount of the acrylic acid employed.

The process according to the invention is carried out in the temperature range from about 50° to about 200° C. Preferably, the temperature range from about 100° to about 150° C. is used.

The process according to the invention can be carried out under normal pressure, under superatmospheric pressure or under reduced pressure. The procedure under superatmospheric pressure can be employed when working at temperatures above the boiling point of acrylic acid. The preferred procedure, in the process according to the invention, is to work under normal (atmospheric) pressure. Generally, the process can be conducted at pressures from 20 Torr to 50 atmospheres.

The process according to the invention can be carried out with or without the use of a solvent. Suitable solvents to employed, where appropriate, are those which are inert under the conditions of the process according to the invention. Examples of solvents which can be mentioned are benzene, toluene, xylene, aliphatic hydrocarbons or mixtures of these, whose boiling points lie within the range of the reaction temperature of the process according to the invention, such as ligroin, as well as ehters, such as dipropyl ehter, dibutyl ether, dioxane or anisole, and also chlorinated hydrocarbons, such as chlorobenzene and dichlorobenzene, or higher-boiling aliphatic or aromatic nitriles, such as benzonitrile.

The process according to the invention is preferably carried out without solvents.

The process according to the invention can be carried out either discontinuously or continuously.

Using the process according to the invention, one can prepare an oligomeric acrylic acid of the formula $$CH_2=CH-COO[CH_2-CH_2-COO]_nH \qquad (I)$$

in which
n represents a number from 1 to 6.
Preferably, an oligomeric acrylic acid or mixture of acids of the formula $$CH_2=CH-COO[CH_2-CH_2-COO]_{n'}H$$

in which
n' represents a number from 1 to 3 is prepared using the process according to the invention.

The following oligomeric acrylic acids may be mentioned as examples: dimeric acrylic acid (β-acryloyloxypropionic acid), and trimeric, tetrameric, pentameric or hexameric acrylic acid.

The oligomeric acrylic acids prepared according to the invention can be freed from the unreacted acrylic acid by distillation. This recovered acrylic acid can, after addition of a polymerization inhibitor, be reintroduced into the process according to the invention.

The oligomeric acrylic acids prepared according to the invention can be worked up by known methods. As such known methods of working up there may be mentioned, for example, distillation or thin layer distillation, if appropriate, under reduced pressure, or extraction.

When working in the lower part of the temperature range according to the invention, or employing a short reaction time, or when both the said conditions apply, β-acryloyloxy-propionic acid is obtained in the main. When working in the upper part of the temperature range according to the invention or when extending the reaction time, or when both conditions apply, oligomeric acrylic acids with a greater chain length can essentially be obtained.

The oligomeric acrylic acids which can be prepared by the process according to the invention are intermediate products for the preparation of polyacrylic acid derivatives. They can be used both for homopolymerization and for copolymerization with other polymerizable compounds.

Amongst the oligomeric acrylic acids which can be prepared according to the invention, β-acryloyloxy-propionic acid, in particular, has been described as an important constituent of adhesives and sealants (DT-OS (German Published Specification) No. 2,529,891), which corresponds to U.S. Pat. No. 4,048,259.

Those adhesives may, for example, consist of a mixture of a methacrylic acid ester, an addition product of hydroxyalkyl methacrylate with an isocyanate prepolymer and β-acryloyloxy-propionic acid.

The adhesive mixtures mentioned need no solvent. They are stable against air and only react as an adhesive on additional admixture of a peroxide by means of a radical polymerisation. This adhering process needs no temperature and not pressure, though a pressure of 1 to 5 bars and/or warming to up to 50° C. accelerates adhering.

The mentioned adhesive mixtures can serve for adhering metals, for example iron, brass, copper or aluminum, glass, ceramics and polymers in any combination.

For the uses mentioned it is also preferable to employ the mixture of oligomeric acrylic acids, of the formula (I), obtained by the process according to the invention. It is an advantage that expensive methods of working up and separation can then be dispensed with.

For the uses mentioned it is also preferred to use mixtures comprising the mixture of oligomeric acrylic acids, of the formula (I), obtainable according to the invention, with the acrylic acid employed. In this case one can, without removing the unconverted acrylic acid, and without further methods of working up and separation, obtain an intermediate product for the uses mentioned, in virtually 100% yield, as reaction product. The content of acrylic acid in such mixtures can vary within the range from 1 to 99% by weight, relative to the total mixture. Preferably, the content of acrylic acid in such mixtures is in the range from 40 to 60% by weight, relative to the total mixture.

The mixtures, obtainable by the process according to the invention, of oligomeric acrylic acids of the formula (I), additionally containing 1–99, preferably 40–60, % by weight of acrylic acid, impart improved flexibility and tensile shear strength to adhesives to which they are added.

EXAMPLE 1

720 g of acrylic acid (10 mols) are warmed for three hours to 138° C. in a reaction vessel. 0.3 g of hydroquinone is used as the stabilizer. After the reaction, the unconverted acrylic acid is distilled off, and can be reused.

A mixture of oligomeric acrylic acids (400 g ≙ 55.5% of theory), consisting to the extent of about 85% of β-acryloyloxy-propionic acid, is obtained. β-Acryloyloxy-propionic acid (boiling point $_{16}$:146°–148° C.) was characterised by the NMR spectrum and by acid titration.

EXAMPLE 2

720 g of acrylic acid stabilised with 0.1 g of phenothiazine are warmed for 30 minutes to 180° C. in an autoclave. After the mixture has cooled, the excess acrylic acid is removed by distillation. A mixture of oligomeric acrylic acids (450 g ≙ 62.5% of theory) remains, which consists of about 45% of β-acryloyloxy-propionic acid, 35% of trimeric acrylic acid and 20% of higher-molecular acrylic acids.

EXAMPLE 3

In a reaction vessel, 720 g of acrylic acid are stabilized with 0.2 g of 4-cyclohexylamino-diphenylamine and warmed for 5 hours to 100° C., with stirring. The unconverted acrylic acid is then distilled off in vacuo and the residue is also distilled in a high vacuum. 370 g of β-acryloyloxy-propionic acid (51.4% of theory) of boiling point 90° C. at 0.08 mm Hg (0.1 mbar) are obtained. The residue (25 g) consists of higher-molecular acrylic acids.

EXAMPLE 4

For the continuous preparation of oligomeric acrylic acids, 360 g of acrylic acid, stabilized with a total of 0.15 g of hydroquinone, are pumped hourly into a reaction vessel heated to 140° C. The reaction product is continuously freed from excess acrylic acid in a thin layer evaporator or falling film evaporator.

Yield: 205 g of oligomeric acrylic acids per hour ( 57% of theory).

EXAMPLE 5

In a reaction vessel, 360 g of acrylic acid are mixed with 300 ml of technical-grade xylene, stabilized with 0.2 g of hydroquinone, and then warmed under reflux for 2 hours. Thereafter, the mixture is subjected to fractional distillation.

Yield: 188 g of oligomeric acrylic acids (≙ 52% of theory), consisting, to the extent of 93%, of dimeric acrylic acid.

EXAMPLE 6

To prepare an adhesive which hardens when oxygen is excluded, a mixture of 62.3 g of the methacrylic acid ester of tetrahydrofurfuryl alcohol, 26.7 g of an addition product of 2 mols of hydroxyethyl methacrylate with a prepolymer obtained from 2 mols of diphenylmethane diisocyanate and a linear polyester (obtained from adipic acid, phthalic acid and diethylene glycol, molecular weight about 2,000), 5.2 g of a mixture of oligomeric acrylic acids (according to Example 2), 5 g of a 70% strength solution of cumene hydroperoxide in cumene and 1 g of tributylamine was mixed.

Steel sheets of size 100×25×1.25 mm, which have been surface-ground in the areas to be glued, are glued together with the above adhesive mixture so as to produce an overlap of about 10 mm. After a storage time of 96 hours at 21° C., the tensile shear strength measured is 2.2 kp/mm$^2$ (DIN 53,283).

What is claimed is:

1. A process for the preparation of a product consisting essentially of an oligomeric acrylic acid or a mixture of oligomeric acrylic acids which acrylic acids have the formula

wherein
n represents a number from 1 to 6 which consists essentially of heating acrylic acid in the presence of 0.001 to 1% by weight of a polymerization inhibitor consisting essentially of molecular oxygen, nitric oxide, a phenol, a quinone, an aromatic amine, a nitro compound or diphenylpicrylhydrazyl in a reaction mixture consisting essentially of said acrylic acid and said polymerization inhibitor to a temperature of about 50° to about 200° C.

2. A process according to claim 1 wherein the acrylic acid is heated to a temperature in the range of 100° to 150° C.

3. A process according to claim 1 wherein there is present 0.02 to 0.1% by weight of polymerization inhibitor.

4. A process according to claim 1 wherein the process is carried out at atmospheric pressure.

5. A process according to claim 1 wherein said polymerization inhibitor is hydroquinone.

6. A process according to claim 1 wherein said polymerization inhibitor is phenothiazine.

7. A process according to claim 1 wherein said polymerization inhibitor is 4-cyclohexylamino-diphenylamine.

* * * * *